United States Patent [19]
Zentner

[11] Patent Number: 4,814,183
[45] Date of Patent: Mar. 21, 1989

[54] DEVICE FOR THE CONTROLLED RELEASE OF DRUGS WITH DONNAN-LIKE MODULATION BY CHARGED INSOLUBLE RESINS

[75] Inventor: Gaylen M. Zentner, Lawrence, Kans.

[73] Assignee: Merck & Co., Inc., Rahway, N.J.

[21] Appl. No.: 91,571

[22] Filed: Aug. 31, 1987

[51] Int. Cl.⁴ .............................................. A61K 9/14
[52] U.S. Cl. .................................. 424/485; 424/486; 424/487; 424/488; 424/443; 424/444
[58] Field of Search ............... 424/486, 487, 485, 488, 424/443, 444

[56] References Cited

U.S. PATENT DOCUMENTS

| 3,854,770 | 11/1974 | Theeuwes et al. | 128/260 |
| 3,916,899 | 11/1975 | Theeuwes et al. | 128/260 |
| 3,993,073 | 11/1976 | Zaffareni | 128/260 |
| 4,160,452 | 7/1979 | Theeuwes | 128/260 |
| 4,200,098 | 4/1980 | Ayer et al. | 128/260 |
| 4,221,778 | 9/1980 | Raghanmethan | 424/31 |
| 4,256,108 | 3/1981 | Theeuwes | 128/260 |
| 4,285,987 | 8/1981 | Ayer et al. | 427/3 |

OTHER PUBLICATIONS

Webster's Third New International Dictionary, Unabridged, Merriam Co., Springfield, Mass. (1961), p. 673.

Primary Examiner—William R. Dixon, Jr.
Assistant Examiner—Andrew Griffis
Attorney, Agent, or Firm—Joseph F. DiPrima; Michael C. Sudol

[57] ABSTRACT

The instant invention is directed to a drug delivery device for the controlled release of beneficial agents and drugs into an environment of use comprising:
(A) a core composition comprising
 (a) a water insoluble, non-diffusible charged resin entity, and
 (b) a diffusible, water soluble ionizable therapeutically active ingredient carrying the same charge as said resin entity; and
(B) a substantially imperforate water-insoluble wall surrounding said core composition, prepared from a semipermeable material substantially impermeable to the core composition and permeable to the passage of an external fluid in the environment of use, with said wall having a hole(s) for release of the therapeutic agent through the water insoluble wall.

20 Claims, 4 Drawing Sheets

DEVICE FOR THE CONTROLLED RELEASE OF DRUGS WITH DONNAN-LIKE MODULATION BY CHARGED INSOLUBLE RESINS

FIELD OF THE INVENTION

This invention pertains to both a novel and useful drug delivery device for dispensing a beneficial agent, hereafter called "drug", to all regions of the gastrointestinal tract, regardless of the pH, at a controlled rate. The invention relates to a drug delivery device comprising a core compartment that contains a charged, water insoluble, non diffusible entity, herein called "charged resin", intimately mixed with a water soluble, diffusible, ionized drug surrounded by a water insoluble semipermeable wall having a release means, herein called "hole(s)". In operation the soluble drug and insoluble resin core components carry the same charge. The device delivers drug at a controlled rate in all regions of the gastrointestinal tract, which has a pH range generally from pH 1 to pH 8. The device thereby presents the beneficial agent to a variable environment of intended use at a controlled rate.

BACKGROUND OF THE INVENTION

The need for systems that can deliver a drug at a controlled rate to a variable environment (e.g. gastrointestinal tract) of use over a specified period of time is well established. The use of novel, charged, water insoluble, non-duffusible resinous powders to modulate drug release from osmotically sensitive devices with rate controlling semipermeable walls that are permeable to water and substantially impermeable to dissolved solutes has not been disclosed in the prior art and represents an advance in drug delivery technology and device composition. U.S. Pat. Nos. 3,854,770 and 3,916,899 disclose devices which have semipermeable walls that are permeable to water and substantially impermeable to dissolved drugs and solutes. A passageway through the semipermeable wall, disclosed as a drilled hole, is provided as an exit portal for the drug through the wall. U.S. Pat. Nos. 4,256,108; 4,160,452; 4,200,098 and 4,285,987 disclose devices which contain multiple wall layers, at least one of said walls having a drilled hole for the release of core components through a rate-controlling semipermeable membrane that is substantially impermeable to dissolved drugs and other solutes. The use of charged resins to modulate drug release from the above devices was not disclosed. U.S. Pat. No. 4,221,778 discloses ion-exchange resin drug complexes as delivery devices where the resin and drug carry opposite charges and osmotic factors are not included; drug release is actuated by exchange of the drug with another ion which dislodges the drug from the resin.

DESCRIPTION OF THE DRAWINGS

Figure 1:
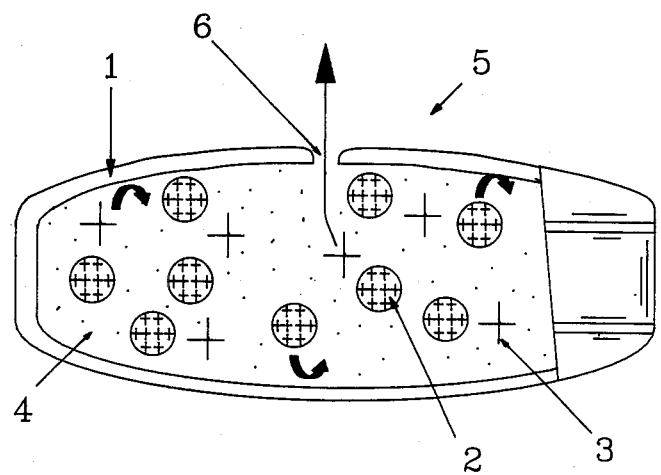
FIG. 1 is a schematic representtion of one embodiment of the instant invention wherein the core composition is surrounded by a substantially imperforate semipermeable, rate-determining, water-insoluble wall which contains a mechanically or optically produced hole(s).
Figure 2:
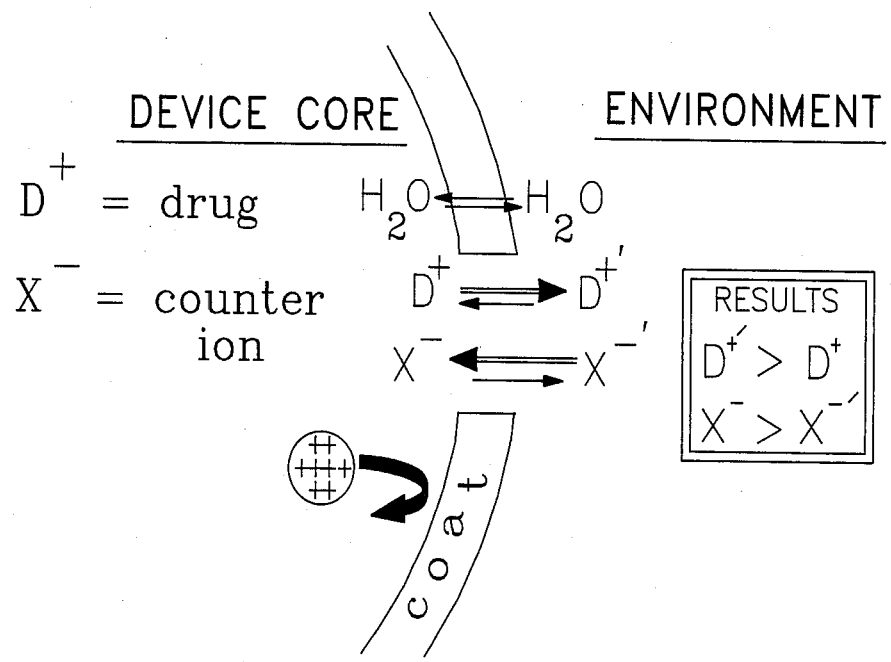
FIG. 2 illustrates that in addition to osmotic flow, the movement of the drug will be subject to Donnan effects which will modulate the release behavior of the drug from the device.

FIG. 1 is a schematic representation of one embodiment of the instant invention. The device, 5, has a core composition comprised of drug species, 3, charged resin(s), 2, and other excipients, 4, as needed to form a tablet suitable for the application of a semipermeable, rate determining, water-insoluble wall, 1, which contains a mechanically or optically produced hole(s), 6, for exit of the drug species from the core. As indicated by the bold arrows, in operation the insoluble resin, 2, will not permeate the wall, 1, or hole, 6, whereas the dissolved drug species, 3, and excipients, 4, are freely released through the hole in response to osmotic and concentration gradients. In the intended environments of use, typically aqueous environments, the drug, 3, and resin, 2, carry the same electrostatic charge. In addition to osmotic flow, the movement of the drug, 3, will be subject to Donnan effects which will modulate the release behavior of the drug from the device in a fashion similar to that illustrated in FIG. 2. Conditions of electrical neutrality dictate an unequal distribution of permeable charged species across any barrier that is selectively impermeable to the charged resin. This phenomena favors the movement of drug bearing a like charge away from the resin, resulting in a modulation of the drug release profile associated with the mass transport effectuating concentration and osmotic gradients.

Figure 1A:
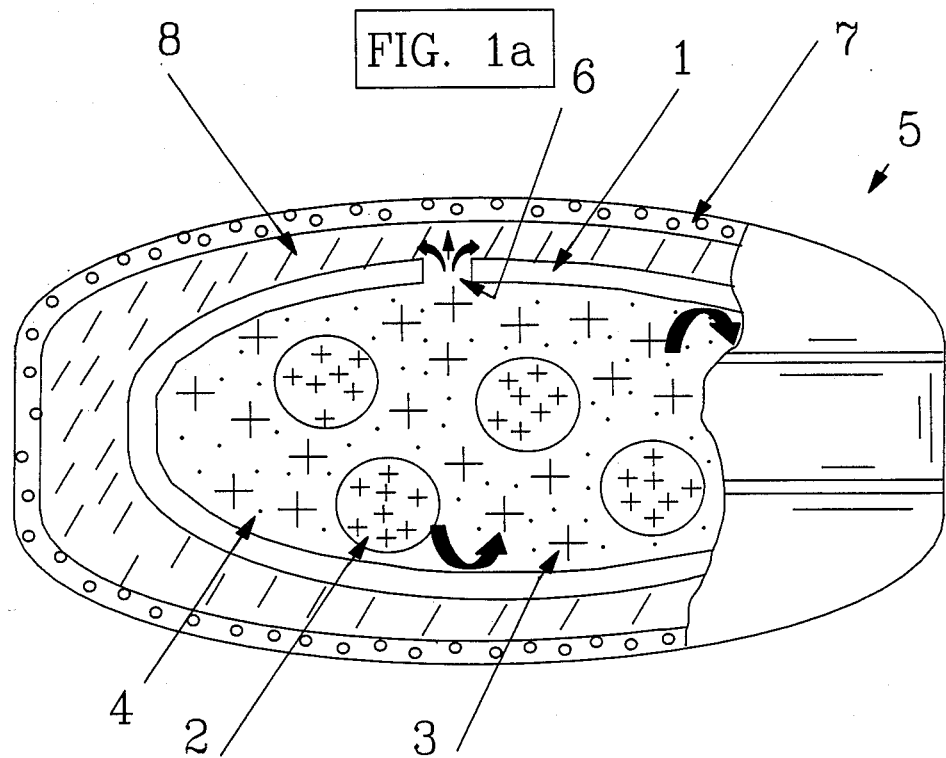
FIG. 1a is another embodiment of the instant invention where the semipermeable wall, 1, is coated with a layer of material, 8, that is soluble in fluids of the intended enverionment of use (commonly water), with a microporous wall, 7, separating the layer, 8, from the external environment.

FIG. 1a is anotherembodiment of the instant invention where the semipermeable wall, 1, is coated with a layer of material, 8, that is soluble in fluids of the intended environment of use (commonly water), with a microporous wall, 7, separating the layer, 8, from the external environment. The compound(s) of layer, 8, dissolve and then freely permeate the microporous wall, 7, in a fluid environment, creating a fluid filled zone separating the microporous and semipermeable walls. Drug laden solution that is pumped through the hole, 6, at a rate controlled by the semipermeable wall, 1, enters the now fluid layer, 8, where it may then freely permeate microporous wall, 7, to the exterior. All other components were defined previously.

Figure 1B:
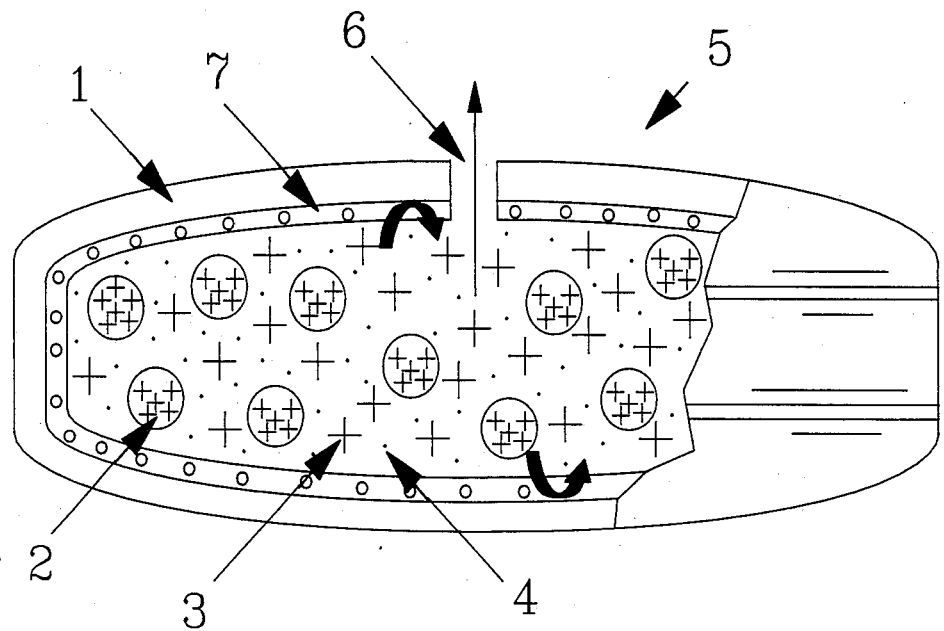
FIG. 1b is another embodiment of the instant invention. As configured, the durg containg core is coated with a laminate structure comprised of a microporous wall, 7, immediately contacting the core, and an overcoating semipermeable wall, 1.

FIG. 1b is another embodiment of the instant invention. As configured, the drug containing core is coated with a laminate structure comprised of a microporous wall, 7, immediately contacting the core, and an overcoating eemipermeable wall, 1. The microporous wall serves as a base coating to lend mechanical strength and support to the rate controlling semipermeable wall. A hole, 6, is provided as an exit portal for the drug solution. Other components were defined previously.

OBJECT OF THE INVENTION

It is an immediate object of this invention to disclose a novel device for delivering drug to produce a beneficial effect. Charged, insoluble, resins bearing an electrostatic charge identical to that of a drug are disclosed for modulation of drug release from a device coated with a semipermeable wall that is breeched by an introduced hole(s).

Another object of the invention is to provide a device for delivering drugs to all parts of the gastrointestinal tract at a substantially constant rate, regardless of the pH of the gastrointestinal tract, through a complex synergistic mechanism that incorporates aspects of diffusion, osmosis, and Donnan like electrostatics.

Another object of the invention is to provide a drug delivery system that is readily manufacturable to deliver a pre determined dose of a drug(s) at a programmed rate from compositions of matter in the varied geometries and sizes of tablets, beads, pellets, multi-particulates, and such related dosage forms as familiar to those skilled in the art for oral, buccal, vaginal, rectal, nasal, ocular, aural, parenteral and related routes of administration.

Anther object of the invention is to provide a drug delivery device for delivering drugs over a range of release rates as controlled by the device, and which device maintains its physical and chemical integrity throughout the release period.

Other objects, features and advantages of the invention will be apparent to those skilled in the art from the following detailed description of the invention taken in conjunction with the drawings and accompanying claims.

BRIEF DESCRIPTION OF THE INVENTION

A device is disclosed for the controlled delivery of a beneficial agent. The agent is delivered to the environment surrounding the device at a substantially constant rate for a specified period with a reduced dependence on the environmental pH. The device is comprised of a core compartment containing, (1) a charged resin and (2) at least one diffusible water soluble ionizable drug. The core is surrounded by a water insoluble wall formed of a semipermeable material substantially impermeable to core components and permeable to the passage of an external fluid in the environment of use, with said wall having a means for release of the beneficial agent(s) through the water insoluble wall. In operation the insoluble charged component (often polymeric resins) and the water soluble ionizable beneficial agent have the same electrostatic charge and do not form an ion exchange complex. Rather, a Donnan influenced mass transport phenomena of the beneficial agent is effected through the release means in the device, actuated by water from the environment, with migration of the freely mobile species (drug) away from the non-mobile species (charged resin). Thus, the device releases the beneficial agent through the release means of the wall at a controlled rate with reduced pH dependency.

DETAILED DESCRIPTION OF THE INVENTION

The instant invention is directed to a drug delivery device for the controlled release of beneficial agents and drugs into an environment of use comprising:
(A) a core composition comprising
 (a) a charged, water insoluble, non-difussible resin entity, and
 (b) a diffusible, water soluble, ionizable therapeutically active ingredient carrying the same charge as said resin entity; and
(B) a water insoluble wall surrounding said core composition, prepared from a substantially imperforate semipermeable material substantially impermeable to the core composition and permeable to the passage of an external fluid in the environment of use, with said wall having a hole(s) for release of the therapeutic agent through the water insoluble wall.

Other microporous walls and soluble layers that are freely permeable to dissolved solutes may be incorporated in conjunction with the semipermeable wall.

The expression water insoluble, non diffusible, charged resin entity as used herein broadly includes any electrostatically charged or electrostatically chargeable species incapable of penetrating through the device wall. Representatives include: (a) cationic resins consisting of polystyrene, epoxy-amine, phenolic or condensate polymeric backbones with varying amounts of cross linkage containing an active group of quaternary ammonium, secondary amine, tertiary amine in an aromatic matrix or tertiary amine in an aliphatic matrix. Examples include Duolite C 20, Wofatit F, Dowex 1, Amberlite IRA-900, Dowex 2, Ionac A-550, and the like; (b) anionic resins with acrylic, methacrylic or phenolic polymeric backbones with phosphonic acid or carboxylic acid active groups such as Dowex CCR-1, Amberlite IRC 50, Zeo Karb 226, and the like; (c) anionic resins with polystyrene or phenolic polymeric backbones with varying degrees of cross linkage containing an active group of sulfonic acid such as Amberlite 200, Dowex 50, Duolite C-3, and the like. An extensive but not limiting list of charged resins can be found in the *Encyclopedia of Polymer Science and Technology*, Volume 7, pp. 692–742, Interscience Pub, Wiley and Sons, 1967.

Another group of charged resins that could be employed have cellulose as the principal support medium and include diethylaminoethyl cellulose, carboxymethyl cellulose, guanidoethyl cellulose, sulfoethyl cellulose, sulfopropyl cellulose and the like. An extensive but not limiting list of charged cellulosics can be found in *The Tools of Biochemistry*, Terrance G. Cooper, p. 143, Wiley and Sons, Inc., 1977.

Another type of charged resin entity includes the cross linked vinylpyridine polymers. At pH 6 or lower the vinylpyridne nitrogen protonates and thus assumes a positive charge. Other charged entities include charged silicates, charged clays, charged earths and zeolites.

The core compartment containing the water soluble drug and water insoluble charged resin, as described herein, is typically in the form of a solid conventional tablet, pellet or particulate. The core is completely encased by the semipermeable wall. The core can be comprised of a mixture of agents combined to give the desired manufacturing and delivery characteristics. The number of agents that may be combined to make the core is substantially without an upper limit with the lower limit equalling two components. It may be useful to buffer the core compartment to keep the electrostatic charge of the drug the same as that of the charged resin.

The preferred specifications for the core are summarized below and include:

1. Core Drug Loading (size)—0.05 nanograms to 5 grams or more (includes dosage forms for humans and animals).

2. Osmotic pressure developed by a solution of the core—8 to 500 atmospheres, typically, with commonly encountered water soluble drugs and excipients; however osmotic pressures greater than zero are within guidelines. 3 Core solubility—continuous, uniform release (zero-order kinetics) of 90% or greater of the initially loaded core mass is theoretically predicted if the ratio of the dissolvable core mass solubility, S, to the dissolvable core mass density, $\rho$, that is $S/\rho$, is 0.1 or lower. Typically this occurs when 10% of the initially loaded dissolvable core mass saturates a volume of external fluid equal to the total volume of the initial dissolvable core mass.

$S/\rho$ ratios greater than 0.1 fall within the workings of the invention and result in lower percentages of initial core mass delivered under zero order kinetics. $S/\rho$ can be selected to give acceptable combined characteristics of stability, release rate, and manufacturability.

4. Water insoluble charged resin component—0.01 to 75% by weight of the total core mass with a charge capacity of 0.01 to 50 mEq/g, preferably 0.01 to 15 mEq/g.

In cases where the drug has the desired solubility, osmotic pressure, density, stability, and manufacturability characteristics, there is no critical upper limit as to the amount that can be incorporated into a core mass and typically will follow the core loading (size) specification 1. The lower limit ratio of drug to excipient is dictated by the desired osmotic attivity of the core composition, the desired time span and profile of release, and the pharmacological activity of the drug. Generally the core will contain 0.01% to 90% by weight or higher, of an active agent in mixture with another solute(s). Representative of compositions of matter that can be released from the device and can function as a solute are, without limitation, those compositions soluble in fluids inside the core compartment as described.

The expression drug as used herein broadly includes any compound, or mixture thereof, that can be delivered from the system to produce a beneficial result. The drug can be soluble in fluid that enters the reservoir and functions as an osmotically effective solute or it can have limited solubility in the fluid and be mixed with an osmotically effective solute(s) that is soluble in fluid that is delivered from the system. The term drug includes pesticides, herbicides, germicides, biocides, algicides, rodenticides, fungicides, insecticides, antioxidants, plant growth promoters, plant growth inhibitors, preservatives, disinfectants, sterilization agents, catalysts, chemical reactants, fermentation agents, foods, food supplements, nutrients, cosmetics, drugs, vitamins, sex sterilants, fertility inhibitors, fertility promoters, air purifiers, microorganism attenuators, and other agents that benefit the environment of use.

In the specification and the accompanying claims, the term "drug" includes any physiologically or pharmacologically active substances that produce a localized or systemic effect or effects in animals, which term includes mammals, humans and primates. The term also includes domestic household, sport or farm animals such as sheep, goats, cattle, horses and pigs, for administering to laboratory animals such as mice, rats and guinea pigs, and to fishes, to avians, to reptiles and zoo animals. The term "physiologically" as used herein denotes the administration of drug to produce normal levels and functions. The term "pharmacologically" denotes the study of the actions of drugs on living systems, including therapeutics, as defined in *Dorland's Illustrated Medical Dictionary*, 1974, Published by W. B. Sanders Co., Philadelphia, Pa. The phrase drug formulation as used herein means the drug and resin are in the compartment, or the drug and resin are in the compartment mixed with an osmotic solute, binder, buffer, dye, mixtures thereof, and the like. The active drug that can be delivered includes inorganic and organic compounds without limitation, including drugs that act on the peripheral nerves, adrenergic receptors, cholinergic receptors, nervous system, skeletal muscles, cardiovascular, smooth muscles, blood circulatory system, synaptic sites, neuroeffector junctional sites, endocrine and hormone systems, immunological system, reproductive system, skeletal system, autocoid systems, alimentary and excretory systems, inhibitory or autocoids and histamine systems, and those materials that act on the central nervous system such as hypnotics and sedatives.

Examples of beneficial drugs are disclosed in *Remington's Pharmaceutical Sciences*, 16th Ed., 1980, published by Mack Publishing Co., Eaton, Pa.; and in *The Pharmacological Basis of Therapeutics*, by Goodman and Gilman, 6th Ed., 1980, published by the MacMillan Company, London; and in *The Merck Index*, 10th Edition, 1983, published by Merck & Co., Rahway, N.J. The dissolved drug can be in various forms, such as charged molecules, charged molecular complexes or ionizable salts. Acceptable salts include, but are not limited to hydrochlorides, hydrobromide, sulfate, laurylate, palmitate, phosphate, nitrate, borate, acetate, maleate, tartrate, oleate, salicylate, salts of metals, and amines or organic cations, for example quaternary ammonium.

Derivatives of drugs such as esters, ethers and amides which have ionization and solubility characteristics suitable for use herein can be used alone or mixed with other drugs. Also, a drug that is water insoluble can be used in a form that is a water soluble ionizable derivative thereof to effectively serve as a solute, and on its release from the device, is converted by enzymes, hydrolyzed by body pH or other metabolic processes to the original form, or to a biologically active form.

Specific examples of drugs that may be adapted for use include pentobarbital sodium, phenobarbital, secobarbital, thiopental and mixtures thereof; heterocyclic hypnotics such as dioxopiperidines and glutarimides; hypnotics and sedatives such as amides and ureas, exemplified by diethyl isovaleramide and $\alpha$-bromoisovaleryl urea; hypnotic and sedative urethanes and disulfanes; psychic energizers such as isocarboxazid, nialamide, phenelzine, imipramine, amitryptyline hydrochloride, tranylcypromine, pargylene, and protryptyline hydrochloride; tranquilizers such as chloropromazine, promazine, fluphenzaine, reserpine, deserpidine, and meprobamate; benzodiazepines such as diazepam and chlordiazepoxide; anticonvulsants such as primidone, phenytoin, and ethosuximide; muscle relaxants and antiparkinson agents such as mephenesin, methocarbomal, cyclobenzaprine hydrochloride, trihexylphenidyl hydrochloride, levodopa/carbidopa, and biperiden; antihypertensives such as a-methyldopa and the pivaloyloxyethyl ester of a-methyldopa; analgesics such as morphine sulfate, codeine sulfate, meperidine, and nalorphine; antipyretics and anti-inflammatory agents such as aspirin, indomethacin, sodium indomethacin trihydrate, salicylamide, naproxen, colchicine, fenoprofen, sulindac, diflunisal, diclofenac, indoprofen and sodium salicylamide; local anesthetics such as procaine, lidocaine, tetracaine and dibucaine; antispasmodics and muscle contractants such as atropine, scopolamine, methsthscopolamine, oxyphenonium, papaverine; prostaglandins such as $PGE_1$, $PGE_2$, $PGF_{2\alpha}$; antimicrobials and antiparasitic agents such as penicillin, tetracycline, oxytetracycline, chlorotetracycline, chloramphenicol, thiabendazole, ivermectin, and sulfonamides; antimalarials such as 4-aminoquinolines, 8-amino-quinolines and pyrimethamine; hormonal and steroidal agents such as dexamethasone, prednisolone, cortisone, cortisol and triamcinolone; androgenic steroids such as methyltestosterone; estrogenic steroids such as 17α-estradiol, α-estradiol, estriol, α-estradiol 3-benzoate, and 17-ethynyl estradiol 3-methyl ether; progestational steroids such as progesterone; s-ympathomimetic drugs such as epinephrine, phenylpropanolamine hydrochloride, amphetamine, ephedrine and norepinephrine; hypotensive drugs such as hydralazine; cardiovascular drugs such as procainamide hydrochloride, amyl nitrite, nitroglycerin, dipyridamole, sodium nitrate and mannitol nitrate; diuretics such as chlorothiazide, acetazolamide, methazolamide, hydrochlorothiazide, amiloride hydrochloride and flumethiazide, sodium ethacrynate, and furosemide; antiparasitics such as bephenium, hydroxynaphthoate, dichlorophen and dapsone; antineoplastics such as mechlorethamine, uracil mustard, 5-fluorouracil, 6-thioquanine and procarbazine; β-blockers such as pindolol, propranolol, metoprolol, oxprenolol, timolol maleate, atenolol; hypoglycemic drugs such as insulin, isophane insulin, protamine zinc insulin suspension, globin zinc insulin, extended insulin zinc suspension, tolbutamide, acetohexamide, tolazamide and chlorpropamide; antiulcer drugs such as cimetidine; nutritional agents such as ascorbic acid, niacin, nicotinamide, folic acid, choline, biotin, pantothenic acid; essential amino acids; essential fats; ophthalmic drugs such as timolol maleate, pilocarpine nitrate, pilocarpine hydrochloride, atropine sulfate, scopolamine; electrolytes such as calcium gluconate, calcium lactate, potassium chloride, potassium sulfate, sodium fluoride, ferrous lactate, ferrous qluconate, ferrous sulfate, ferrous fumurate and sodium lactate; and drugs that act on α-adrenergic receptors such as clonidine hydrochloride.

Additional preferred drugs include quinoline and naphthyridine carboxylic acids and related compounds, such as norfloxacin.

Additional preferred drugs include budesonide, enprofylline, tranilast, albuterol, theophylline, aminophylline, brompheniramine, chlorpheniramine, promethazine, diphenhydramine, azatadine, cyproheptadine, terbutaline, metaproternol, and isoproterenol; drugs which are antidepresessants such as doxepin, trazodone; antipsychotic drugs such as haloperidol, thioridazine, trifluoperazine; sedative hypnotic and antianxiety drugs such as triazolam, temazepam, chlorazepate, alprazolam, diazepam, flurazepam, lorazepam, oxazepam, hydroxyzine, prazepam, meprobamate, butalbital, and chlorzoxazone; antiparkinson drugs such as benztropine and noxazinol; hormonal and steroidal drugs such as conjugated estrogens, diethylstilbesterol, hydroxy progesterone, medroxy proqestrone, norethindrone, betamethasone, methylprednisolone, prednisone, thyroid hormone, and levothyroxine; antihypertensive and cardiovascular drugs such as isosorbide dinitrate, digoxin, nadolol, disopyramide, nifedipine, quinidine, lidocaine, diltiazem hydrochloride, verapamil, prazosin, captopril, enalapril, lisinopril, metyrosine, felodipine, tocainide, mexiletine, mecamylamine, and metyrosine; diuretic drugs such as spironolactone, chlorthalidone, metolazone, triamterene, methyclothiazide, and indacrinone; antiinflammatory drugs such as ibuprofen, ibuprofen lysinate, phenylbutazone, tolmetin, piroxicam, melclofenamate, auranofin, flurbiprofen and penicillamine; analgesic drugs such as acetaminophen, oxycodone, hydrocodone, and propoxyphene; antiinfective drugs such as cefoxitin, cefazolin, cefotaxime, cephalexin, nicarbazin, amprolium, ampicillin, amoxicillin, cefaclor, erythromycin, nitrofurantoin, minocycline, doxycycline, cefadroxil, miconazole, clotrimazole, phenazopyridine, clorsulon, fludalanine, pentizidone, cilastin, phosphonomycin, imipenem, arprinocid, and foscarnet; gastrointestinal drugs such as bethanechol, clidinium, dicyclomine, meclizine, prochlorperizine, trimethobenzamide, loperamide, ranitidine, diphenoxylate, famotidine, metoclopramide and omeprazole; anticoagulant drugs such as warfarin, phenindione, and anisindione; and other drugs such as trientine, cambendazole, ronidazole, rafoxinide, dactinomycin, asparaginase, nalorphine, rifamycin, carbamezepine, metaraminol bitartrate, allopurinol, probenecid, diethylpropion, dihydrogenated ergot alkaloids, nystatin, pentazocine, phenylpropanolamine, phenylephrine, pseudoephedrine, trimethoprim, lovastatin, eptastatin, simvastatin, ivermectin, and milbemycin.

The above list of drugs is not meant to be exhaustive. Many other drugs will certainly work in the instant invention.

The drug can be in the core compartment as a solution, dispersion, paste, cream, particle, granule, emulsion, suspension or powder. Also, the drug can be mixed with a binder, dispersant, emulsifier or wetting agent and dyes.

The amount of drug, or drug admixed with other osmotically active solutes and buffers present in the device, is generally initially in excess of the amount that can be dissolved in the fluid that enters the reservoir. Under this physical state when the drug is in excess and combined with resin, the device will osmotically operate with Donnan-like modulation to give a substantially constant rate of release. The drug release pattern can also be varied by having different amounts of drug in the reservoir to form solution containing different concentrations of agent for delivery from the device. Generally, the device can house from 0.05 ng to 5 grams drug or more, with individual devices containing, for example, 25 ng, 1 mg, 5 mg, 250 mg, 500 mg, 1.5 g and the like.

Mixtures of drug with other pH modifying and/or osmotically active compounds may be used to attract fluid into the device producing a solution of compound which is delivered from the device, concomitantly transporting drug to the exterior of the device. Examples include but are not limited to magnesium sulfate, magnesium chloride, sodium chloride, lithium chloride, potassium sulfate, sodium carbonate, potassium carbonate, potassium bicarbonate, sodium sulfite, lithium sulfate, potassium chloride, calcium bicarbonate, sodium sulfate, sodium bicarbonate, sodium bitartrate, citric acid, adipic acid, potassium or sodium mono- or di-phosphate, calcium lactate, d-mannitol, urea, inositol, sorbitol, pentaerythritol, magnesium succinate, magnesium oxide, magnesium hydroxide, tromethamine, tartaric acid, carbohydrates such as raffinose, sucrose, glucose, α-d-lactose monohydrate, mixtures thereof, and the like. The compound may be present in excess and it can be in any physical form such as particle, crystal, pellet, tablet, strip, film or granule.

The rate controlling wall of the invention is a material that is semi-permeable, can form films, and does not adversely affect the drug, animal body, or host, for example, a material that is permeable to an external fluid such as water and the like while essentially impermeable to a selected product, drugs, agents, resins or to other compounds in the device. The selectively-permeable material or membrane forming the wall is insoluble in body fluids and non-erodible or it can be bioerodible after a predetermined period with bioerosion corresponding to the end of the active drug release period. In each instance it is semipermeable to solvent but not to solute and resin and is suitable for construction of the osmotic powered device. Typical materials for forming the wall include membranes known to the art as osmosis and reverse osmosis membranes. Generally, membranes having a fluid permeability of 0.01 to 10 cc/cm$^2$X hour or day/or higher at atmospheric pressure against a saturated product solution or saturated solute solution at the temperature of use while simultaneously possessing a high degree of impermeability to the product or solute are useful for manufacturing the devices of the invention. Of course, other semi-permeable membranes operable for the purposes of the invention can also be used within the spirit of the invention.

Additional, preferred specifications for the semipermeable wall include:

1. Plasticizers and Flux Regulating Additives: 0 to 50, preferably 0.001 to 50, parts per 100 parts wall material.
2. Surfactant Additives: 0 to 40, preferably 0.001 to 40, parts per 100 parts wall material.
3. Wall Thickness: 1 to 1,000, preferably 20 to 500, microns typically, although thinner and thicker fall within the invention.

Any polymer permeable to water but impermeable to solutes as previously defined may be used. Examples include cellulose acetate having a degree of substitution, D.S., meaning the average number of hydroxyl groups on the anhydroglucose unit of the polymer replaced by a substituting group, up to 1 and acetyl content up to 21%; cellulose diacetate having a D.S. of 1 to 2 and an acetyl content of 21 to 35%; cellulose triacetate having a D.S. of 2 to 3 and an acetyl content of 35 and 44.8%; cellulose propionate having an acetyl content of 1.5 to 7% and a propionyl content of 2.5 to 3% and an average combined propionyl content of 39.2 to 45% and a hydroxyl content of 2.8 to 5.4%; cellulose acetate butyrate having a D.S. of 1.8, an acetyl content of 13 to 15%, and a butyryl content of 34 to 39%; cellulose acetate having an acetyl content of 2 to 99.5%, a butyryl content of 17 to 53%, and a hydroxyl content of 0.5 to 4.7%; cellulose triaceylates having a D.S. of 2.9 to 3 such as cellulose trivalerate, cellulose trilaurate, cellulose tripalmitate, cellulose trisuccinate, cellulose triheptylate, cellulose tricaprylate, cellulose trioctanoate, and cellulose tripropionate; cellulose diesters having a lower degree of substitution and prepared by the hydrolysis of th corresponding triester to yield cellulose diacylates having a D.S. of 2.2 to 2.6 such as cellulose dicaprylate and cellulose dipentanate; and esters prepared from acyl anhydrides or acyl acids in an esterification reaction to yield esters containing different acyl groups attached to the same cellulose polymer such as cellulose acetate valerate, cellulose acetate succinate, cellulose propionate succinate, cellulose acetate octanoate, cellulose valerate palmitate, cellulose acetate palmitate and cellulose acetate heptanoate.

Additional polymers that can be used for the purpose of the invention include cellulose acetate acetoacetate, cellulose acetate chloroacetate, cellulose acetate furoate, dimethoxyethyl cellulose acetate, cellulose acetate carboxymethoxypropionate, cellulose acetate benzoate, cellulose butyrate naphthylate, cellulose acetate benzoate, methyl cellulose acetate, methylcyanoethyl cellulose, cellulose acetate methoxyacetate, cellulose acetate ethoxyacetate, cellulose acetate dimethylsulfamate, ethylcellulose, ethylcellulose dimethylsulfamate, cellulose acetate p-toluene sulfonate, cellulose acetate methylsulfonate, cellulose acetate dipropylsulfamate, cellulose acetate butylsulfonate, cellulose acetate laurate, cellulose stearate, cellulose acetate methylcarbamate, agar acetate, amylose triacetate, beta glucan acetate, beta glucan triacetate, acetaldehyde dimethyl acetate, cellulose acetate ethyl carbamate, cellulose acetate phthalate, cellulose acetate dimethyl aminoacetate, cellulose acetate ethyl carbonate, poly (vinyl methyl) ether copolymers, cellulose acetate with acetylated hydroxyethylcellulose, cellulose, hydroxylated ethylenevinylacetate, poly(ortho ester)s, polyacetals, semipermeable polyglycolic or polylactic acid and derivatives thereof, film forming materials with a water sorption of one to fifty percent by weight at ambient temperatures with a presently preferred water sorption of less than thirty percent, acylated polysaccharides, acylated starches, aromatic nitrogen containing polymeric materials that exhibit permeability to aqueous fluids, membranes made from polymeric epoxides, copolymers of alkylene oxides and alkyl glycidyl ethers, polyurethanes, polyacrylate and polymethacrylate polymers, and derivatives and the like. Admixtures of various polymers may also be used.

The polymers described are known to the art or they can be prepared according to the procedures in *Encyclopedia of Polymer Science and Technology*, Vol. 3, pages 325 to 354, and 459 to 549, published by Interscience Publishers, Inc., New York, in *Handbook of Common Polymers* by Scott, J. R. and Roff, W. J., 1971, published by CRC Press, Cleveland, Ohio; and in U.S. Pat. Nos. 3,133,132; 3,173,876; 3,276,586; 3,541,055; 3,541,006; and 3,546,142.

The expression "release means" or hole(s) as used herein are comprised of those means and methods suitable for osmotically releasing the drug from the core through the semipermeable wall.

The expression includes the following: an aperture, orifice, bore, porous element through which product can migrate, hollow cellulose acetate fibers suitable for passing the drug, capillary tubes, cracks, and the like. The expression also includes bioerodible materials that erode in the environment of use to produce an osmotic passageway of precontrolled dimensions. Typical bioerodible materials suitable for forming a passageway include erodible poly(glycolic) acid and poly(lactic) acid fibers, poly(ortho esters), erodible gelatinous filaments, poly(vinyl alcohol), and the like.

Water insoluble, permeable, non-rate controlling microporous walls may be applied to core composition masses prior to the application of the semipermeable wall or subsequent thereto by spray coating procedures. The microporous wall may either directly contact the semipermeable wall to form a bilaminate structure, or, the microporous wall may be separated from the semipermeable wall by a layer of fluid soluble material, which may optionally contain drug, which dissolves in the environment of use, creating a fluid layer separating the microporous and semipermeable walls. This microporous wall is comprised of (a) polymeric material that is insoluble in the fluids of the environment of intended use (usually water), (b) other added excipients that will dissolve in the environmental fluids or leach out of the wall. The leached wall is a sponge-like structure composed of numerous open and closed cells that form a discontinuous interwoven network of void spaces when viewed with a scanning electron microscope. The wall is permeable to both water and solutes, and as constituted in the environment of use has a small solute reflection coefficient, $\nu$, and displays poor semipermeable characteristics when placed in a standard osmosis cell. Additional specifications for the microporous wall include:

1. Wall Thickness: 1 to 1,000, preferably 20 to 500, microns typically although thinner and thicker fall within the invention.

2. Pore Forming Additives: 0.1 to 75%, by weight, based on the total weight of pore forming additive and polymer, pore forming additive, preferably: (a) 0.1 to 50% by weight solid additive; (b) 0 1 to 40% by weight liquid additive.

A controlled porosity wall can be generically described as having a sponge-like appearance. The pores can be continuous pores that have an opening on both faces of a microporous lamina, pores interconnected through tortuous paths of regular and irregular shapes including curved, curved-linear, randomly oriented continuous pores, hindered connected pores and other porous paths discernible by microscopic examination. Generally, microporous lamina are defined by the pore size, the number of pores, the tortuosity of the microporous path and the porosity which relates to the size and number of pores. The pore size of a microporous lamina is ascertained by measuring the observed pore diameter at the surface of the material under the electron microscope. Generally, materials possessing from 5% to 95% pores and having a pore size of from 10 angstroms to 100 microns can be used.

Pore forming additives may be used in the instant invention. The microporous wall may be formed in situ, by a pore-former being removed by dissolving or leaching it to form the microporous wall during the operation of the system. The pores may also be formed in the wall prior to operation of the system by gas formation within curing polymer solutions which result in voids and pores in the final form of the wall. The pore-former can be a solid or a liquid. The term liquid, for this invention embraces semi-solids, and viscous fluids. The pore-formers can be inorganic or organic. The pore-formers suitable for the invention include pore-formers that can be extracted without any chemical change in the polymer. Solid additives include alkali metal salts such as sodium chloride, sodium bromide, potassium chloride, potassium sulfate, potassium phosphate, sodium benzoate, sodium acetate, sodium citrate, potassium nitrate and the like; the alkaline earth metal salts such as calcium chloride, calcium nitrate, and the like; the transition metal salts such as ferric chloride, ferrous sulfate, zinc sulfate, cupric chloride, and the like. Water may be used as the pore-former. The pore formers include organic compounds such as dimethyl sulfone, nicotinamide, saccharides and amino acids. The saccharides include the sugars sucrose, glucose, fructose, mannose, galactose, aldohexose, altrose, talose, lactose, monosaccharides, disaccharides, and water soluble polysaccharides. Also, sorbitol, pentaerythritol, mannitol, organic aliphatic and aromatic ols, including diols and polyols, as exemplified by polyhydric alcohols, poly(alkylene glycols), polyglycols, alkylene glycols, poly($\alpha$, $\omega$)alkylenediols esters or alkylene glycols, polyvinylalcohol, poly vinyl pyrrolidone, and water soluble polymeric materials. Pores may also be formed in the wall by the volatilization of components in a polymer solution or by chemical reactions in a polymer solution which evolves gases prior to application or during application of the solution to the core mass resulting in the creation of polymer foams serving as the porous wall of the invention. The pore-formers are nontoxic, and on their removal channels are formed that fill with fluid. The channels become a transport path for fluid. In a preferred embodiment, the non-toxic pore-forming agents are selected from the group consisting of water soluble inorganic and organic compounds and salts, carbohydrates, polyols, polyalkylene glycols, poly($\alpha$, $\omega$)alkylenediols, esters of alkylene glycols, and glycols, that are used in a biological environment.

The microporous materials can be made by etched nuclear tracking, by cooling a solution of flowable polymer below the freezing point with subsequent evaporation of solvent to form pores, by gas formation in a polymer solutinn which upon curing results in pore formation, by cold or hot stretching at low or high temperatures until pores are formed, by leaching from a polymer a soluble component by an appropriate solvent, by ion exchange reaction, and by polyelectrolyte processes. Processes for preparing microporous materials are described in *Synthetic Polymer Membranes: A Structural Perspective*, 2nd Ed., by R. E. Kesting, Chapters 7 and 8, 1985, published by John Wiley & Sons, Inc.; *Chemical Reviews*, Ultrafiltration, Vol. 18, pages 373 to 455, 1934; *Polymer Eng. and Sci.*, Vol. 11, No. 4, pages 284 to 288, 1971, *J. Appl. Poly. Sci.*, Vol. 15, pages 811 to 829, 1971, and in U.S. Pat. Nos. 3,565,259; 3,615,024; 3,751,536; 3,801,692; 3,852,224; and 3,849,528.

It is generally desirable from a preparation standpoint to mix the polymers which will comprise either the semipermeable or microporous walls in a solvent. Exemplary solvents suitable for manufacturing the wall of the instant device include inert inorganic and organic solvents that do not adversely harm the core, wall, and the materials forming the final wall. The solvents broadly include members selected from the group consisting of aqueous solvents, alcohols, ketones, esters, ethers, aliphatic hydrocarbons, halogenated solvents, cycloaliphatic, aromatics, heterocyclic solvents and mixtures thereof. Typical solvents include acetone, diacetone alcohol, methanol, ethanol, isopropyl alcohol, butyl alcohol, methyl acetate, ethyl acetate, isopropyl acetate, n-butyl acetate, methyl isobutyl ketone, methyl ethyl ketone, methyl propyl ketone, n-hexane, ethyl lactate, n-heptane, ethylene glycol monoethyl ether, ethylene glycol monoethyl acetate, methylene dichloride, ethylene dichloride, propylene dichloride, carbon tetrachloride, nitroethane, nitropropane, tetrachloroethane, ethyl ether, isopropyl ether, cyclohexane, cyclooctane, dimethylbromamide, benzene, toluene, naphtha, 1,4-dioxane, tetrahydrofuran, diglyme, water, and mixtures thereof such as acetone and water, acetone and methanol, acetone and ethyl alcohol, methylene dichloride and methanol, and ethylene dichloride and methanol. Illustrative of mixed solvents are acetone methanol (80:20), acetone-ethanol (90:10), methylene dichloridemethanol (80:20), ethyl acetate-ethanol (80:20), ethylene dichloride-methanol (80:20), methylene dichloride-methanol (50:50), methylene dichloride-methanol (78:22), acetone-water (90:10), chloroform-ethanol (80:20), methylene dichloride-ethanol (79:21), methylene chloride-methanol-water (15:10:1), carbon-tetrachloride-methanol (70:30), expressed as (weight:- weight), and the like. Water based latex forms of suitable polymers are also within the guidelines of the invention.

Exemplary plasticizers suitable for the present wall forming purposes include plasticizers that lower the temperature of the second order phase transition of the wall or the elastic modulus thereof, and also increase the workability of the wall and its flexibility. Plasticizers may increase or decrease the permeability of the wall to fluids including water and aqueous solutions. Plasticizers operable for the present purpose include both cyclic plasticizers and acyclic plasticizers. Typical plasticizers are those selected from the group consisting of phthalates, phosphates, citrates, adipates, tartrates, sebacates, succinates, glycolates, glycerolates, benzoates, myristates, polyethylene glycols, polypropylene glycols, and halogenated phenyls. Generally, from 0.001 to 50 parts of a plasticizer or a mixture of plasticizers are incorporated into 100 parts of wall forming material.

Exemplary plasticizers include dialkyl phthalates, dicycloalkyl phthalates, diaryl phthalates and mixed alkylaryl as represented by dimethyl phthalate, dipropyl phthalate, dioctyl phthalate, di-(2-ethyl-hexyl)-phthalate, di-isopropyl phthalate, diamyl phthalate and dicapryl phthalate; alkyl and aryl phosphates such as triethyl phosphate, tributyl phosphate, trioctyl phosphate, tricresyl phosphate and triphenyl phosphate; alkyl citrate and citrate esters such as tributyl citrate, triethyl citrate, and acetyl triethyl citrate; alkyl adipates such as dioctyl adipate, diethyl adipate and di-(2-methyoxyethyl)-adipate; dialkyl tartrates such as diethyl tartrate and dibutyl tartrate; alkyl sebacates such as diethyl sebacate, dipropyl sebacate and dinonyl sebacate; alkyl succinates such as diethyl succinate and dibutyl succinate; alkyl glycolates, alkyl glycerolates, glycol esters and glycerol esters such as glycerol diacetate, glycerol triacetate, glycerol monolactate diacetate, methyl phthalyl ethyl glycolate, butyl phthalyl butyl glycolate, ethylene glycol diacetate, ethylene glycol dibutyrate, triethylene glycol dibutyrate and triethylene glycol dipropionate. Other plasticizers include polyethylene glycol 400, polyethylene glycol 20,000, camphor, N-ethyl-(o- and p-toluene) sulfonamide, chlorinated biphenyl, benzophenone, N-cyclohexyl-p-toluene sulfonamide, and substituted epoxides.

Suitable plasticizers can be selected for blending with the wall forming materials by selecting plasticizers that have a high degree of solvent power for the materials, are compatible with the materials over both the processing and use temperature range, exhibit permanence as seen by their tendency to remain in the plasticized wall, impart flexibility to the material and are non-toxic to animals, humans, avians, fishes and reptiles. Procedures for selecting a plasticizer having the described characteristics are disclosed in the *Encyclopedia of Polymer Science and Technology*, Vol. 10, pages 228 to 306, 1969, published by John Wiley & Sons, Inc. Also, a detailed description pertaining to the measurement of plasticizer properties including solvent parameters and compatibility such as the Hildebrand solubility parameter $\delta$, the Flory-Huggins interaction parameter $\chi$, and the cohesive energy density, CED, parameters are disclosed in *Plasticization and Plasticizer Processes*, Advances in Chemistry Series 48, Chapter 1, pages 1 to 26, 1965, published by the American Chemical Society. The amount of plasticizer added generally is an amount sufficient to produce the desired wall and it will vary according to the plasticizer and the other wall forming materials. Usually about 0.001 part up to 50 parts of plasticizer can be used for 100 parts of wall material.

The expressions "flux regulator agent", "flux enhancing agent" and "flux decreasing agent" as used herein mean a compound that when added to a wall forming material assists in regulating the fluid permeability (flux) through the wall. The agent can be preselected to increase or decrease the fluid flux. Agents that produce a marked increase in permeability to a fluid such as water, are often essentially hydrophilic, while those that produce a marked decrease in permeability to fluids such as water, are often essentially hydrophobic. The flux regulators in some embodiments also can increase the flexibility and porosity of the lamina. Examples of flux regulators include polyhydric alcohols and derivatives thereof, such as polyalkylene glycols of the formula H-(O-alkylene)$_n$-OH wherein the bivalent alkylene radical is straight or branched chain and has from 1 to 10 carbon atoms and n is 1 to 500 or higher. Typical glycols include polyethylene glycols 300, 400, 600, 1500, 1540, 4000 and 6000 of the formula H-(OCH$_2$CH$_2$)$_n$-OH wherein n is typically 5 to 5.7, 8.2 to 9.1, 12.5 to 13.9, 29 to 36, 29.8 to 37, 68 to 84, and 158 to 204, respectively. Other polyglycols include the low molecular weight glycols of polypropylene, polybutylene and polyamylene.

Additional flux regulators include poly ($\alpha, \omega$) alkylenediols wherein the alkylene is straight or branched chain of from 2 to 10 carbon atoms such as poly(1,3)-propanediol, poly(1,4) butanediol, poly(1,5)pentanediol and poly(1,6)hexanediol. The diols also include aliphatic diols of the formula HOC$_n$H$_{2n}$OH wherein n is from 2 to 10 and diols are optionally bonded to a non-terminal carbon atom such as 1,3-butylene glycol, 1,4-pentamethylene glycol, 1,5-hexamethylene glycol and 1,8-decamethylene glycol; and alkylenetriols having 3 to 6 carbon atoms such as glycerine, 1,2,3-butanetriol, 1,2,3-pentanetriol, 1,2,4-hexanetriol and 1,3,6-hexanetriol.

Other flux regulators include esters and polyesters of alkylene glycols of the formula HO-(alkylene-O)$_n$-H wherein the divalent alkylene radical includes the straight chain groups and the isomeric forms thereof having from 2 to 6 carbons and n is 1 to 14. The esters and polyesters are formed by reacting the glycol with either a monobasic or dibasic acid or anhydride. Exemplary flux regulators are ethylene glycol dipropionate, ethylene glycol butyrate, ethylene glycol diacetate, triethylene glycol diacetate, butylene glycol dipropionate, polyester of ethylene glycol with succinic acid, polyester of diethylene glycol with maleic acid, and polyester of triethylene glycol with adipic acid.

The amount of flux regulator added to a material generally is an amount sufficient to produce the desired permeability, and it will vary according to the lamina forming material and the flux regulator used to modulate the permeability. Usually from 0.001 parts up to 50 parts, or higher of flux regulator can be used to achieve the desired results.

Surfactants useful for the present wall forming purpose are those surfactants, when added to a wall forming material and other materials, aid in producing an integral composite that is useful for making the operative wall of a device. The surfactants act by regulating the surface energy of materials to improve their blending into the composite. The composite material is used for manufacturing devices that maintain their integrity in the environment of use during the agent release period. Generally, the surfactants are amphipathic molecules comprised of a hydrophobic part and a hydrophilic part. The surfactants can be anionic, cationic, nonionic or amphoteric. The anionic surfactants include sulfated, sulfonated, or carboxylated esters, amides, alcohols, ethers, aromatic hydrocarbons, aliphatic hydrocarbons, acylated amino acids and peptides. Metal alkyl phosphates are another class of anionic surfactant. Typically, cationic surfactants are primary, secondary, tertiary or quaternary alkylammonium salts, acylated polyamines, and salts of heterocyclic amines. Nonionic surfactants are typically esters and ethers of polyoxyalkylene glycols, polyhydric alcohols, or phenols. Poloxamers are included as nonionic surfactants. Ampholytic molecules such as betaine are also surfactants. Surfactants are discussed in *Surfactant Systems, Their Chemistry, Pharmacy, and Biology*, D. Attwood and A. T. Florence, Chapman and Hall Pub. Co., 1983, pgs 1–8.

Examples of surfactants include potassium laurate, sodium dodecyl sulfate, hexadecylsulphonic acid, sodium dioctylsulphosuccinate, hexadecyl(cetyl)trimethylammonium bromide, dodecylpyridinium chloride, dodecylamine hydrochloride, N-dodecyl-N,N-dimethyl betaine, bile acids and salts, acacia, tragacanth, Iqepal, sorbitan esters (Spans), polysorbates (Tweens), Triton-X analogs, Brij analogs, Myrj analogs, pluronics, tetronics, surface active drug agents such as phenothiazines and tricyclic antidepressants, and the like.

Suitable surfactants can be selected from the above and from other surfactants for blending with wall forming materials by using the surfactant's hydrophile lipophile balance number, HLB. This number represents the proportion between the weight percentages of hydrophilic and lipophilic groups in a surfactant. In use, the number indicates the behavior of the surfactant, that is, the higher the number the more hydrophilic the surfactant and the lower the number the more lipophilic the surfactant. The required HLB number for blending wall forming materials is determined by selecting a surfactant with a known HLB number, blending it with the materials and observing the results. A uniform composite is formed with the correct HLB number, while a non-uniform mixture indicates a different number is needed. This new number can be selected by using the prior HLB number as a guide. The HLB number is known to the art for many surfactants, and they can be experimentally determined. Generally a HLB number of 10 or less indicates lipophilic behavior and 10 or more indicates hydrophilic behavior. Also, HLB numbers are algebraically additive. Thus, by using a low number with a high number, blends of surfactant can be prepared having numbers intermediate between the two numbers. The concept of HLB is detailed in *Remington's Pharmaceutical Sciences*, 16th Ed., Mack Pub. Co., (1980), pages 316–319. The amount of surfactant needed is an amount that when blended with wall forming materials will form the desired wall composite, and it will vary according to the particular surfactant and materials that are blended to form the wall. Generally, the amount of surfactant will range from about 0.001 part up to 40 parts for 100 parts of wall.

The layer of fluid soluble material which may be positioned between a semipermeable wall containing a hole(s) and a microporous wall, comprises a layer of material selected from organic or inorganic compounds that are soluble in the fluid of the environment of use; drug may optionally be included. Fluid entering the system (commonly water) dissolves the layer to form a solution which is released to the exterior through the microporous wall. Drug laden solution exiting the hole(s) in the semipermeable wall enters this fluid layer at a rate controlled by the semipermeable wall from where the drug is released to the exterior through the microporous wall. Representative inorganic compounds that can be used for forming the layer include magnesium chloride, sodium chloride, lithium chloride, potassium chloride, sodium carbonate, potassium carbonate, manganese carbonate, sodium sulfite, potassium sulfite, lithium sulfite, magnesium sulfate, calcium bicarbonate, sodium bicarbonate, potassium bicarbonate, sodium sulfite, potassium sulfite, lithium sulfite, magnesium sulfite, potassium acid phosphate, sodium acid phosphate, and the like. Typical organic compounds include carbohydrates such as glucose, sucrose, fructose, raffinose and lactose, and other organic compounds soluble in water and biological fluids such as mannitol, inositol, urea, magnesium succinate, tartaric cid, and the like.

The following examples illustrate the preparation of the drug delivery devices of this invention and their controlled release of one or more therapeutically active ingredients into an environment of use and as such are not to be considered as limiting the invention set forth in the claims appended hereto.

EXAMPLES

In the following examples diltiazem hydrochloride is used as the model drug. The pKa of diltiazem hydrochloride is 7.7. In the devices described below the core compartment is buffered to keep the pH below 6 to keep diltiazem and the resins positively charged.

EXAMPLE b 1

A plurality of drug delivery systems containing Dowex 1 (8% cross linked, 200–400 mesh) as a positively charged (quaternary ammonium) resin are prepared as follows: a wet granulation is made containing diltiazem hydrochloride, pentaerythritol, Dowex 1, citric acid, and adipic acid mixed 2:10:4:1:1, respectively. 10% w/w polyvinylpyrrolidone (29–32K) is used as a binder. Core tablets are prepared by compressing 600 mg aliquots (60 mg drug load) of the dried granulation into a 5/16″ standard concave tabletting die by applying a 2 ton force with a single station hydraulic press. Next, the semipermeable wall is applied to these cores. 36 g cellulose acetate having an acetyl content of 32% and 36 g cellulose acetate having an acetyl content of 39% are dissolved in a dichloromethane/methanol solvent blend. To this is added 20 g polyethylene glycol 400 as a flux enhancer/plasticizer dissolved in a water/methanol solvent blend. The composite solution contains water:methanol:dichloromethane in an approximate 1:10:15 ratio. This solution is sprayed onto the cores in a commercial Uni-Glatt fluidized bed coating machine. A wall 100 to 200 microns thick is applied. A hole 0.15 mm in diameter is drilled.

EXAMPLE 2

A plurality of drug delivery devices are prepared with diltiazem HCl and the positively charged insoluble resin poly-4-vinylpyridine hydrochloride. The vinylpyridine nitrogen becomes protonated, and thus positively charged, at pH 6 or less. Citric acid and adipic acid are incorporated into the core compartment to maintain the pH below 6 inside the core compartment during operation, thus maintaining both the resin and drug in the positively charged state. A wet granulation is made containing 11% w/w diltiazem hydrochloride, 56% w/w pentaerythritol, 10% w/w poly-4-vinylpyridine hydrochloride, 6.5% w/w citric acid, 6.5% w/w adipic acid and 10% w/w polyvinylpyrrolidone (29–32K). Core compartments are prepared by compressing 540 mg aliquots (60 mg drug load) of the dried granules into a 5/16" standard concave tabletting die as in Example 1. Next, the semipermeable wall is applied to these core compartments. A coating solution identical to that of Example 1 is applied as in Example 1. An 0.15 mm diameter hole is drilled.

EXAMPLE 3

A plurality of drug delivery devices are prepared with diltiazem HCl and the positively charged insoluble resin poly-4-vinylpyrridine hydrochloride. A wet granulation is made containing 9.5% w/w diltiazem hydrochloride, 48% w/w pentaerythritol, 21% w/w poly-4-vinylpyridine hydrochloride, 5.5% w/w citric acid, 5.5% w/w adipic acid and 10.5% w/w polyvinylpyrrolidone (29–32K). Core compartments are made by compressing 636 mg aliquots (60 mg drug load) of the dried granules into a 5/16" standard concave tabletting die as in Example 1. Next, a microporous wall is applied. 72 g cellulose acetate having an acetyl content of 39% is dissolved in a dichloromethane/methanol solvent blend. To this is added 54 g. nicotinamide as pore former and 40 g polyethylene glycol 400 as a flux enhancer/plasticizer dissolved in methanol. This solution is sprayed onto the cores in a Uni-Glatt fluidized bed coating machine to form a microporous wall 200 microns thick. This microporous wall is then covered by a semipermeable wall as described in Example 1 with a hole 0.15 mm in diameter drilled through both the microporous and semipermeable walls.

EXAMPLE 4

A plurality of drug delivery devices are prepared with diltiazem HCl and the positively charged insoluble resin poly-4-vinylpyrridine hydrochloride. A wet granulation is made containing 9.5% w/w diltiazem hydrochloride, 48% w/w pentaerythritol, 21% w/w poly-4-vinylpyridine hydrochloride, 5.5% w/w citric acid, 5.5% w/w adipic acid and 10.5% w/w polyvinylpyrrolidone (29–32K). Core compartments are made by compressing 636 mg aliquots (60 mg drug load) of the dried granules into a 5/16" standard concave tabletting die as in Example 1.

The cores are coated with a semipermeable wall 200 microns thick containing a drilled 0.15 mm diameter hole as described in Example 1. The devices are then spray coated with a 110 micron thick layer of a water soluble mixture of polyvinyl pyrrolidone and sorbitol mixed in a 1:25 weight ratio. This layer is then covered by a microporous wall 100 microns thick by spray coating a dichloromethane/methanol/water solution of a 1:1:1 blend of cellulose acetate having an acetyl content of 32%, cellulose acetate having an acetyl content of 39%, and sorbitol. The sorbitol is incorporated as a pore forming additive.

What is claimed is:

1. A drug-delivery device for the controlled release of therapeutically active ingredient into an environment of use which comprises:
   (A) a core composition comprising
      (a) a water insoluble, non-diffusible charged resin entity, and
      (b) a diffusible water soluble ionizable therapeutically active ingredient carrying the same charge as said resin entity; and
   (B) a substantially imperforate water insoluble wall surrounding said core composition and prepared from a semipermeable material substantially impermeable to core composition and permeable to the passage of an external fluid in the environment of use, with said wall having a means for release of the therapeutic agent through the water insoluble wall.

2. A drug-delivery device according to claim 1, wherein the resin entity is a cationic resin selected from the group consisting of polystyrene, epoxy-amine, phenolic or condensate polymeric backbones containing an active group of quaternary ammonium, secondary amine, tertiary amine in an aromatic matrix or tertiary amine in an aliphatic matrix.

3. A drug-delivery device according to claim 1, wherein the resin entity is an anionic resin with acrylic, methacrylic or phenolic polymeric backbones with phosphonic acid or carboxylic acid active groups.

4. A drug-delivery device according to claim 1, wherein the resin entity is an anionic resin with polystyrene or phenolic polymeric backbones containing an active group of sulfonic acid.

5. A drug-delivery device according to claim 1, wherein the resin entity is a cellulose polymer selected from the group consisting of diethylamino-ethyl cellulose, carboxymethyl cellulose, guanidoethyl cellulose, sulfoethyl cellulose, and sulfopropyl cellulose.

6. A drug-delivery device according to claim 1, wherein the resin entity is a cross-linked vinyl pyridine polymer.

7. A drug-delivery device according to claim 1, wherein the therapeutically active ingredient is soluble in an external fluid and exhibits an osmotic pressure gradient across the wall against the external fluid.

8. A drug-delivery device according to claim 1, wherein the therapeutically active ingredient has limited solubility in the external fluid and is mixed with an osmotically effective solute that is soluble in the fluid, which exhibit an osmotic pressure gradient across the wall against the external fluid.

9. A drug-delivery device according to claim 1, further comprising:
   (C) 0 to 50 parts per 100 parts of wall material, of plasticizer and flux regulating additives and
   (D) 0 to 40 parts per 100 parts of wall material, of surfactant additive.

10. A drug-delivery device according to claim 1, wherein said water insoluble wall is 1 to 1,000 microns thick.

11. A drug-delivery device according to claim 10 wherein said wall is 20 to 500 microns thick.

12. A drug-delivery device according to claim 1, wherein at least 0.05 ng of active agent are used.

13. A drug-delivery device according to claim 12, wherein at least 1 microgram of active agent is used.

14. A drug-delivery device according to claim 1, wherein said semipermeable material is selected from the group consisting of cellulose esters, acylated polysaccharides, polyurethane, polymers of acrylic and methacrylic acid and esters thereof, poly (ortho ester)s, polyacetals and mixtures thereof.

15. A drug-delivery device according to claim 14, wherein said semipermeable material is selected from the group consisting of cellulose esters and acylated polysaccharides.

16. A drug-delivery device according to claim 15, wherein said semipermeable material is selected from the group consisting of polyurethanes and polymers of acrylic and methacrylic acid and esters thereof.

17. A drug-delivery device according to claim 15, wherein said semipermeable material is selected from the group consisting of poly(ortho esters)s and polyacetals.

18. A drug-delivery device according to claim 1, further comprising a water insoluble, permeable, non-rate controlling microporous wall.

19. A drug-delivery device according to claim 18, wherein the microporous wall is separated from the semipermeable wall by a layer of fluid soluble material.

20. A drug-delivery device according to claim 18, wherein the microporous wall is in direct contact with the semipermeable wall.

* * * * *